United States Patent [19]

Lassmann et al.

[11] 4,299,337
[45] Nov. 10, 1981

[54] PULSED SYRINGE FOR USE WITH ELECTRON-SPIN-RESONANCE SPECTROMETERS AND THE LIKE

[75] Inventors: Günter Lassmann; Bernd Ebert; Norbert Klimes, all of Berlin, German Democratic Rep.

[73] Assignee: Akademie der Wissenschaften der DDR, Berlin, German Democratic Rep.

[21] Appl. No.: 15,779

[22] Filed: Feb. 28, 1979

[30] Foreign Application Priority Data

Mar. 2, 1978 [DD] German Democratic Rep. ... 203936

[51] Int. Cl.³ .............................................. B67D 5/44
[52] U.S. Cl. ...................... 222/135; 91/35; 222/391
[58] Field of Search ...................... 310/17, 23, 24, 30; 91/35, 37; 222/135, 391; 74/128, 160, 578

[56] References Cited

U.S. PATENT DOCUMENTS

| | | | |
|---|---|---|---|
| 3,161,323 | 12/1964 | Bent | 222/391 X |
| 3,161,325 | 12/1964 | Hinkel et al. | 222/391 X |
| 3,354,708 | 11/1967 | Joron | 74/578 X |
| 3,790,048 | 2/1974 | Luciano et al. | 74/128 X |
| 3,908,862 | 9/1975 | Chandra et al. | 222/135 X |

*Primary Examiner*—David A. Scherbel
*Attorney, Agent, or Firm*—Michael J. Striker

[57] ABSTRACT

A pulsed-flow apparatus for spectrometers and the like has a mixing chamber and two syringes each adapted to contain a different liquid and both connected to the mixing chamber. The plunger of each syringe has an outwardly extending rod provided with a toothed rack. A pair of electric armatures are provided, each reciprocable lengthwise of one of the rods and carrying a pressure spring which moves with the armature and, during each move of the armature towards the syringe, advances the plunger deeper into the syringe by the length of one tooth of the rack, but does not extract it when the armature subsequently moves in the opposite direction.

5 Claims, 2 Drawing Figures

PULSED SYRINGE FOR USE WITH ELECTRON-SPIN-RESONANCE SPECTROMETERS AND THE LIKE

BACKGROUND OF THE INVENTION

1. Field of the Invention

The invention concerns a pulsed mixing and flow apparatus particularly designed for electron-spin-resonance (ESR) spectrometers.

2. Description of the Prior Art

Known mixing apparatus for optical spectroscopy, the Aminco stopped-flow spectrometers (USA), data sheet (1974), uses a mechanically rigid coupling between flow system and flow cell, which, on stopping the liquid during ESR spectroscopy, leads to strong microphony disturbances and thus could cause false measurements. Stopped-flow ESR apparatus (by J. C. KERTECZ and W. WOLF Journal of Physics E: Sci. Instr. (1973) 6 1009) has also been provided with a pneumatic flow system and with costly solenoid valves. The large amounts of substances required (100 ml–1000 ml) make it practically impossible to justify an operation with costly biological substances that are only available in small amounts.

SUMMARY OF THE INVENTION

It is the objective of the invention to develop a flow apparatus that with limited expenditure, will allow ESR investigations of biological specimens and the like in an aqueous environment, will not generate spurious microphony signals, will preclude metallic contact of the solutions in the system and will permit simple cleaning of all parts.

This objective and others which will become apparent hereinafter is achieved by the use of a solenoid to pulse a piston that forces fluid out of a reservoir. The core of the solenoid is moved when the solenoid is energized and de-energized, and is connected to the piston by means of a toothed rack and the slip collar. The rack and the collar are so designed that when the solenoid core is moved in one direction the piston is advanced, while when the solenoid core is moved in an opposite direction the piston is not retracted. As a result, a series of pulses will empty the reservoir in a series of steps.

Preferably, the solenoid can be energized by means of a capacitor which can discharge into the solenoid core and which is controlled by use of a thyristor. Because of the shape of a typical capacitor discharge curve, the maximum rate of discharge occurs in the initial stages of the capacitor's discharge, generating a strong pulse that enables the inertia of the liquid in the reservoir to be overcome.

In this invention, two liquids can be mixed together with great force when each liquid is delivered from an individual pulsed syringe. Since like capacitors and like thyristors can be used, it is possible to precisely control the pulsing of the syringes utilized so as to cause the fluid to be pulses simultaneously.

The solenoid core is spring-biased so that the pulses delivered to the solenoid coils need only be in one direction. Retraction of the solenoid core is thus accomplished by means of a spring and not by reverse polarization of the solenoid.

As a result of the useage of such a solenoid, and the use of the toothed rack and the slip collar, the previously necessary solenoid valves and stopping syringes are obviated. Moreover, problems with synchronization of the opening and closing of the solenoid valves such as are present in known apparatus, cannot occur in this invention.

In order to eliminate spurious microphony signals, flexible Teflon tubing may be used to connect the reservoir in which the liquid to be mixed is stored to the mixing cell. Thus, by utilizing this invention, short-lived radicals and spin-tagged biopolymers can be subjected to ESR spectrometry without the generation of spurious microphony signals. Moreover, metallic contact of the solutions within the system is prevented and all parts of the system can be cleaned very simply. Moreover, the syringes may easily be manufactured of such a size that small samples can be analyzed. A syringe manufactured according to the principles of this invention can also be utilized in optical spectrometry and in conductivity measurements.

DETAILED DESCRIPTION OF PREFERRED EMBODIMENTS

Figure 1:
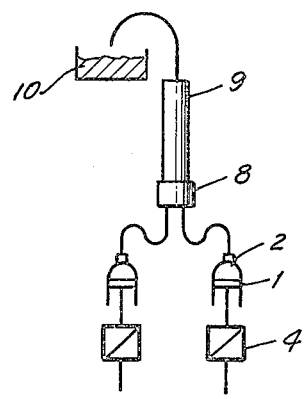
FIG. 1 shows a schematic diagram of an ESR spectrometer supplied by syringes manufactured according to the principles of this invention.

The flow apparatus schematically shown in FIG. 1 consists of two polyethylene injection syringes, whose pistons 1 are connected to cores 6 of solenoids 4 via toothed racks with teeth 3 and the pressure spring 5. The syringes are connected with the mixing cell 8 and the flow cell 9 by flexible Teflon tubing 12. A catch vessel 10 for the effluent liquid is arranged above flow cell 9.

Figure 2:
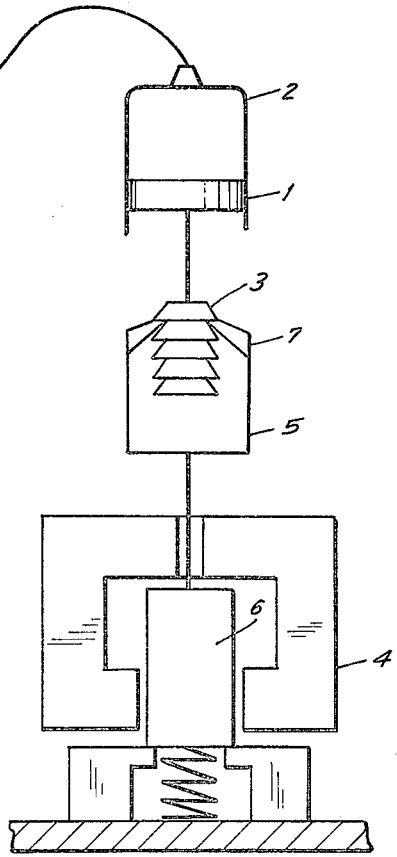
FIG. 2 is an exploded elevational view of the invention.

In this apparatus, the solenoids, energized by controlled capacitor discharge, will generate the impulses for moving the two syringes. Strokes of the cores 6 of about 1 mm length are transferred, via pressure, springs to toothed racks attached to the pistons of the syringes. As shown in FIG. 2, when the core 6 moves upwardly, the pressure spring 5 pushes the rack 3 and piston 1 upwardly, while when the retracting spring 11 moves the core 6 downwardly, the claws 7 expand to slip down one tooth on the rack. Thus, repeated advances of the rack will occur as the solenoid is pulsed. Energization of the solenoid is controlled by thyristors and ensues by the discharge of a 150 $\mu$F capacitor, (600 V) though the solenoid coil. Liquid is then forced out of the syringe under the pressure of the piston and through the flexible tubing into the mixing cell 8 and will then reach the flow cell 9 which is mounted rigidly on the mixing cell 8.

The mixing cell 8 is made of Plexiglass and has bores for feed and discharge. The flow cell 9 is constructed as a thick-walled (3 mm) flat quartz cell in order to prevent bursting during the pressure impulse caused in the liquid by the stroke of the armature. The flexible supply tubing and the fixed setting of the mixing and flow cell within the resonator preclude disturbances caused by transmitting the pressure impulse to the ESR proving system. The number of impulses per syringe charge depends upon the effective volume of the syringes. With an effective volume of 1 ml each, 10 pressure impulses of 0.1 ml each are, for instance, possible.

Since one pressure impulse will force the fourfold volume (200 µl) of one flow cell filling (48 µl) through the latter, complete evacuation of the old cell contents and steady-state conditions prior to stopping, will be achieved.

When the syringe disclosed herein is used with an ESR spectrometer, a 2 millisecond time resolution can be achieved.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A pulsed-flow apparatus for mixing quantities of two liquids in preparation for further processing, comprising means defining a mixing chamber; a pair of housings chambers being adapted to contain a different liquid; conduit means connecting each of said reservoir chambers with said mixing chamber; a piston in each housing and movable into the respective reservoir chamber to expel liquid therefrom via said conduit means, and a piston rod extending from each piston out of the respective housing; a pair of toothed racks each mounted on one of said piston rods for movement therewith; a pair of reciprocable electric armatures each movable back and forth lengthwise of one of said piston rods; a pressure spring on each armature, movable therewith and engaging one of said racks to advance the same and thereby the piston thereof into the associated reservoir chamber when the armature moves in one direction, but to prevent retraction of the rack and piston when the armature moves in the opposite direction; and means for moving the respective armatures in pulsed fashion.

2. An apparatus as defined in claim 1, each of said armatures being a core in a solenoid which has a coil surrounding the core.

3. An apparatus as defined in claim 2, wherein each of said armatures includes a retraction spring urging the core in said opposite direction.

4. An apparatus as defined in claim 1, each of said housings together with the associated piston constituting a syringe.

5. An apparatus as defined in claim 1, wherein said means includes a capacitor and a thyristor, the thyristor controlling discharge of the capacitor into the respective coil.

* * * * *